(12) United States Patent
Zhuang et al.

(10) Patent No.: US 11,865,258 B2
(45) Date of Patent: Jan. 9, 2024

(54) DATA PROCESSING METHOD AND DEVICE BASED ON POSITIVE PRESSURE VENTILATION THERAPY MACHINE

(71) Applicant: BMC MEDICAL CO., LTD., Beijing (CN)

(72) Inventors: Zhi Zhuang, Beijing (CN); Weifeng Liu, Beijing (CN)

(73) Assignee: BMC MEDICAL CO., LTD., Beijing (CN)

( * ) Notice: Subject to any disclaimer, the term of this patent is extended or adjusted under 35 U.S.C. 154(b) by 832 days.

(21) Appl. No.: 16/770,393

(22) PCT Filed: Dec. 6, 2018

(86) PCT No.: PCT/CN2018/119482
§ 371 (c)(1),
(2) Date: Jun. 5, 2020

(87) PCT Pub. No.: WO2019/109965
PCT Pub. Date: Jun. 13, 2019

(65) Prior Publication Data
US 2020/0384225 A1    Dec. 10, 2020

(30) Foreign Application Priority Data
Dec. 7, 2017    (CN) .......................... 201711286775.X

(51) Int. Cl.
*A61M 16/00* (2006.01)
(52) U.S. Cl.
CPC ...... *A61M 16/024* (2017.08); *A61M 16/0003* (2014.02); *A61M 16/0066* (2013.01);
(Continued)

(58) Field of Classification Search
CPC .............. A61M 16/00; A61M 16/0003; A61M 16/0066; A61M 16/024;
(Continued)

(56) References Cited

U.S. PATENT DOCUMENTS

| 5,740,795 A | * | 4/1998 | Brydon | ............... A61M 16/024 128/204.23 |
| 2002/0005197 A1 | * | 1/2002 | DeVries | ............... A61M 16/202 128/204.21 |

(Continued)

FOREIGN PATENT DOCUMENTS

| CN | 101060878 A | 10/2007 |
| CN | 103736183 A | 4/2014 |

(Continued)

*Primary Examiner* — Joseph D. Boecker
(74) *Attorney, Agent, or Firm* — Volpe Koenig

(57) ABSTRACT

A data processing method and device based on a positive pressure ventilation therapy machine is described. The method comprises: acquiring a current operating parameter and a current pressure value of a draught fan in the positive pressure ventilation therapy machine; finding a target relational expression corresponding to the current pressure value in a preset list according to the current pressure value, wherein the preset list comprises a plurality of pressure values and relational expressions corresponding to the plurality of pressure values, and each of the relational expressions corresponding to the plurality of pressure values is a relational expression between operating parameters of the draught fan and a gas flow output by the positive pressure ventilation therapy machine; and determining a current gas flow output by the positive pressure ventilation therapy machine according to the current operating parameter and the target relational expression.

8 Claims, 2 Drawing Sheets

(52) U.S. Cl.
CPC ............... *A61M 2016/003* (2013.01); *A61M 2016/0027* (2013.01); *A61M 2205/3334* (2013.01)

(58) Field of Classification Search
CPC .... A61M 2016/0027; A61M 2016/003; A61M 2205/3334; A61M 16/0057; G16H 40/63
See application file for complete search history.

(56) References Cited

U.S. PATENT DOCUMENTS

| | | | |
|---|---|---|---|
| 2006/0065270 A1* | 3/2006 | Li | A61M 16/026 |
| | | | 128/204.23 |
| 2008/0216833 A1 | 9/2008 | Pujol et al. | |
| 2008/0257348 A1* | 10/2008 | Piper | A61M 16/0069 |
| | | | 128/205.25 |
| 2009/0044805 A1 | 2/2009 | Somaiya et al. | |
| 2013/0312750 A1* | 11/2013 | Farrugia | F04D 27/001 |
| | | | 128/204.21 |
| 2016/0243325 A1 | 8/2016 | Bowman et al. | |
| 2017/0361041 A1* | 12/2017 | Scheerer | A61M 16/0066 |
| 2019/0224432 A1* | 7/2019 | Hamilton | A61M 16/024 |

FOREIGN PATENT DOCUMENTS

| | | |
|---|---|---|
| CN | 104288881 A | 1/2015 |
| CN | 104524676 A | 4/2015 |
| DE | 202017003149 U1 | 8/2017 |
| DE | 202017003149 U1 | 9/2017 |
| WO | 2006047826 A1 | 5/2006 |
| WO | 2016157104 A1 | 10/2016 |

\* cited by examiner

DATA PROCESSING METHOD AND DEVICE BASED ON POSITIVE PRESSURE VENTILATION THERAPY MACHINE

CROSS REFERENCE TO RELATED APPLICATIONS

This application is a 35 USC § 371 national stage of, PCT/CN2018/119482, which was filed Dec. 6, 2018, claims priority to Chinese Application No. 201711286775.X, filed on Dec. 7, 2017, and is entitled "DATA PROCESSING METHOD AND APPARATUS BASED ON POSITIVE PRESSURE VENTILATION THERAPY MACHINE," both of which are incorporated herein by reference as if fully set forth.

FIELD OF THE INVENTION

The present invention relates to the technical field of data processing and specifically relates to a data processing method and device based on a positive pressure ventilation therapy machine.

BACKGROUND OF THE INVENTION

When a positive pressure ventilation therapy machine is used, it is required that a gas flow output by the positive pressure ventilation therapy machine is recorded and an Apnea-Hypopnea Index (AHI) is calculated according to the gas flow, so that whether the current parameter setting of the positive pressure ventilation therapy machine is appropriate can be judged according to the AHI, and furthermore, further adjustment is provided. At present, the gas flow is generally acquired by adopting a flow sensor, however, for customers, a therapy machine with the flow sensor is overhigh cost, which results in overhigh burden.

SUMMARY OF THE INVENTION

Embodiments of the present invention aim at providing a data processing method and device based on a positive pressure ventilation therapy machine to solve the problem of overhigh cost of a flow sensor adopted in the prior art and reduce the cost.

In order to achieve the above-mentioned purpose, an embodiment of the present invention provides a data processing method based on a positive pressure ventilation therapy machine, comprising: acquiring a current operating parameter and a current pressure value of a draught fan in the positive pressure ventilation therapy machine; finding a target relational expression corresponding to the current pressure value in a preset list according to the current pressure value, wherein the preset list comprises a plurality of pressure values and relational expressions corresponding to the plurality of pressure values, and each of the relational expressions corresponding to the plurality of pressure values is a relational expression between operating parameters of the draught fan and a gas flow output by the positive pressure ventilation therapy machine; and determining a current gas flow output by the positive pressure ventilation therapy machine according to the current operating parameter and the target relational expression. According to the embodiment of the present invention, the problem that the cost of the positive pressure ventilation therapy machine is increased due to the demand of installing a flow sensor for measuring the gas flow is solved. In addition, in the prior art, the gas flow is measured by adopting two pressure sensors instead of the flow sensor, which can also increase the additional expense, however, in the embodiment of the present invention, the current pressure value detected by a pressure sensor existing in the prior art is utilized, and the current gas flow output by the positive pressure ventilation therapy machine is determined according to the current operating parameter and the current pressure value of the draught fan as well as the preset list, so that the cost of the flow sensor specially used for measuring the gas flow and required by the positive pressure ventilation therapy machine is reduced, and the burden of a patient is relieved.

Further, the current operating parameter is a current current value or a current voltage value. Compared with the prior art in which a way of calculating the gas flow according to the rotating speed and pressure value of the draught fan is adopted to result in the situation of inaccurate simulation for the gas flow when a characteristic curve of the draught fan is not monotonous, the embodiment of the present invention has the advantages that the rotating speed and electromagnetic torque of the draught fan have monotonicity under the condition that the voltage or current of the draught fan is unchanged, and the electromagnetic torque can be in direct proportion to the gas flow, so that the relation between the gas flow and the voltage or current of the draught fan is approximate to a logarithmic relation, and the accuracy of the gas flow obtained according to the above-mentioned relation can be guaranteed.

Further, the step of determining the current gas flow output by the positive pressure ventilation therapy machine according to the current operating parameter and the target relational expression comprises: performing calculation according to $$F = \frac{1}{B}\ln\left(\frac{P}{K}\right)$$

to obtain the current gas flow output by the positive pressure ventilation therapy machine, wherein F is the gas flow, P is the current operating parameter, B and K are conversion coefficients, and the conversion coefficients are related to the current pressure value. The above-mentioned calculation way is relatively simple and convenient in software implementation under the condition that the error range is taken into account as much as possible.

Further, the method further comprises the steps of finding two relational expressions corresponding to two pressure values adjacent to the current pressure value in the preset list and determining the two relational expressions as a first relational expression and a second relational expression when the current pressure value is not found in the preset list; determining a first gas flow and a second gas flow according to the current operating parameter, the first relational expression and the second relational expression; and determining a mean value of the first gas flow and the second gas flow as the current gas flow output by the positive pressure ventilation therapy machine. A gas flow corresponding to a pressure value not existing in the preset list can also be obtained in a linear relation fitting way in the embodiment of the present invention, so that the application range of the embodiment of the present invention is widened.

An embodiment of the present invention further provides a data processing device based on a positive pressure ventilation therapy machine, comprising: an acquiring unit, used for acquiring a current operating parameter and a current pressure value of a draught fan in the positive pressure ventilation therapy machine; a finding unit, used for finding a target relational expression corresponding to the current pressure value in a preset list according to the current pressure value, wherein the preset list comprises a plurality of pressure values and relational expressions corresponding to the plurality of pressure values, and each of the relational expressions corresponding to the plurality of pressure values is a relational expression between operating parameters of the draught fan and a gas flow output by the positive pressure ventilation therapy machine; and a determining unit, used for determining a current gas flow output by the positive pressure ventilation therapy machine according to the current operating parameter and the target relational expression. According to the embodiment of the present invention, the problem that the cost of the positive pressure ventilation therapy machine is increased due to the demand of installing a flow sensor for measuring the gas flow is solved. In addition, in the prior art, the gas flow is measured by adopting two pressure sensors instead of the flow sensor, which can also increase the additional expense, however, in the embodiment of the present invention, the current pressure value detected by a pressure sensor existing in the prior art is utilized, and the current gas flow output by the positive pressure ventilation therapy machine is determined according to the current operating parameter and the current pressure value of the draught fan as well as the preset list, so that the cost of the flow sensor specially used for measuring the gas flow and required by the positive pressure ventilation therapy machine is reduced, and the burden of a patient is relieved.

Further, the current operating parameter acquired by the acquiring unit is a current current value or a current voltage value. Compared with the prior art in which a way of calculating the gas flow according to the rotating speed and pressure value of the draught fan is adopted to result in the situation of inaccurate simulation for the gas flow when a characteristic curve of the draught fan is not monotonous, the embodiment of the present invention has the advantages that the rotating speed and electromagnetic torque of the draught fan have monotonicity under the condition that the voltage or current of the draught fan is unchanged, and the electromagnetic torque can be in direct proportion to the gas flow, so that the relation between the gas flow and the voltage or current of the draught fan is approximate to a logarithmic relation, and the accuracy of the gas flow obtained according to the above-mentioned relation can be guaranteed.

Further, the determining unit is further used for performing calculation according to $$F = \frac{1}{B}\ln\left(\frac{P}{K}\right)$$

to obtain the current gas flow output by the positive pressure ventilation therapy machine, wherein F is the gas flow, P is the current operating parameter, B and K are conversion coefficients, and the conversion coefficients are related to the current pressure value. The above-mentioned calculation way is relatively simple and convenient in software implementation under the condition that the error range is taken into account as much as possible.

Further, the finding unit is further used for finding two relational expressions corresponding to two pressure values adjacent to the current pressure value in the preset list and determining the two relational expressions as a first relational expression and a second relational expression when the current pressure value is not found in the preset list; and the determining unit is further used for determining a first gas flow and a second gas flow according to the current operating parameter, the first relational expression and the second relational expression and determining a mean value of the first gas flow and the second gas flow as the current gas flow output by the positive pressure ventilation therapy machine.

An embodiment of the present invention further provides a data processing device based on a positive pressure ventilation therapy machine, comprising a processor, a memory and a computer program stored in the memory and capable of operating on the processor, and the computer program implements the above-mentioned data processing method based on the positive pressure ventilation therapy machine when being executed by the processor.

An embodiment of the present invention further provides a computer readable storage medium, storing a computer program, and the computer program implements the above-mentioned data processing method based on the positive pressure ventilation therapy machine when being executed by a processor.

According to the above-mentioned technical solution, the current operating parameter and the current pressure value of the draught fan in the positive pressure ventilation therapy machine are acquired, the target relational expression corresponding to the current pressure value is found in the preset list according to the current pressure value, and the current gas flow output by the positive pressure ventilation therapy machine is determined according to the current operating parameter and the target relational expression. According to the embodiments of the present invention, the problem of overhigh cost of the flow sensor adopted in the prior art is solved, and the cost is reduced.

Other characteristics and advantages of the embodiments of the present invention will be described in detail in the subsequent detailed descriptions.

DESCRIPTION OF THE DRAWINGS

The drawings are provided for further understanding the embodiments of the present invention, construct a part of the specification and are intended to explain the embodiments of the present invention together with the following detailed descriptions, rather than to limit the embodiments of the present invention. In the accompanying drawings.

DETAILED DESCRIPTION OF THE EMBODIMENTS

The detailed descriptions of the embodiments of the present invention are described in detail below in combination with accommodating drawings. It should be understood that the detailed descriptions described herein are only intended to describe and explain the embodiments of the present invention, rather than to limit the embodiment of the present invention.

A draught fan in a positive pressure ventilation therapy machine is a power device of the positive pressure ventilation therapy machine and can provide a gas flow with a certain pressure, and a mechanical characteristic of the draught fan can be expressed by a formula (1).

$$n = \frac{30}{\pi R K_e K_T} \cdot \frac{K_T U_d - R T_e}{1} \quad \text{formula (1)}$$

Wherein n is the rotating speed of the draught fan, $K_T$ is a torque coefficient, $U^d$ is the voltage of the draught fan, R is the resistance of the draught fan, $T_e$ is an electromagnetic torque, and $K_e$ is a back electromotive force coefficient. Known from the formula (1), a mechanical characteristic curve of the draught fan is shown as FIG. 1, in addition, the rotating speed and electromagnetic torque in the draught fan have monotonicity under the condition that the voltage of the draught fan is unchanged.

Figure 1:
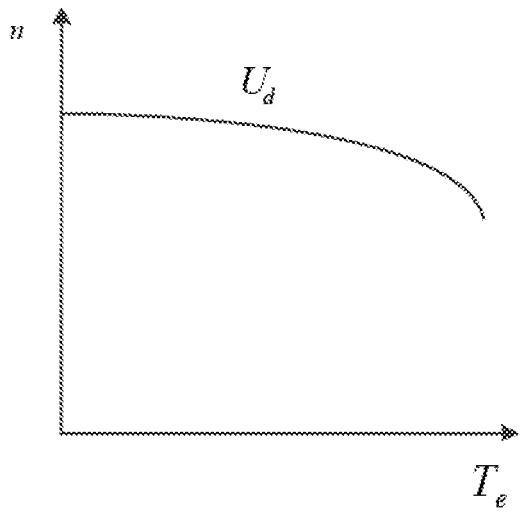
FIG. 1 is a mechanical characteristic curve diagram of a draught fan.

Known from a formula (2), the electromagnetic torque is:

$$T_e = \frac{EI}{\omega} \quad \text{formula (2)}$$

Wherein E is a back electromotive force of a winding, I is a current of the winding, and ω is an angular speed. According to energy conservation, energy generated by the electromagnetic torque is further provided as a pressure and energy for the gas flow output by the positive pressure ventilation therapy machine in addition to being used for self-loss. When the pressure is approximate to be constant, the electromagnetic torque is further in direct proportion to the gas flow. Known from the mechanical characteristic curve of the draught fan as shown in FIG. 1, a relation between the gas flow and the voltage or current of the draught fan is approximate to a logarithmic relation under the condition that the pressure is approximate to be constant. Therefore, the gas flow is calculated according to the operating parameter and pressure value of the draught fan in the embodiment of the present invention.

Figure 2:
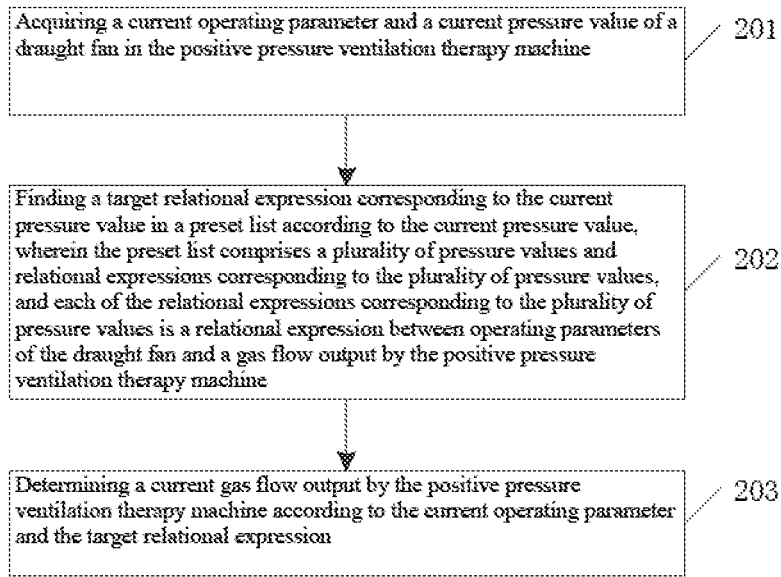
FIG. 2 is a flow chart of a data processing method based on a positive pressure ventilation therapy machine provided by an embodiment of the present invention.

FIG. 2 is a flow chart of a data processing method based on a positive pressure ventilation therapy machine provided by an embodiment of the present invention. As shown in FIG. 2, the method comprises the following steps:

Step 201, a current operating parameter and a current pressure value of a draught fan in the positive pressure ventilation therapy machine are acquired.

The operating parameter and pressure value of the draught fan can be acquired in real time. The pressure value can be acquired in real time by virtue of a pressure sensor arranged in the positive pressure ventilation therapy machine in the prior art. In addition, there is a requirement on a single fault in general requirements (IEC60601) of medical equipment, the current operating parameter of the draught fan, such as the current current value or current voltage value of the draught fan, can be detected by the positive pressure ventilation therapy machine in the prior art. Therefore, the current operating parameter and the current pressure value of the draught fan in the positive pressure ventilation therapy machine can be easily acquired. Compared with the prior art in which a way of calculating the gas flow according to the rotating speed and pressure value of the draught fan is adopted to result in the situation of inaccurate simulation for the gas flow when a characteristic curve of the draught fan is not monotonous, the embodiment of the present invention has the advantages that the rotating speed and electromagnetic torque of the draught fan have monotonicity under the condition that the voltage or current of the draught fan is unchanged, and the electromagnetic torque can be in direct proportion to the gas flow, so that the relation between the gas flow and the voltage or current of the draught fan is approximate to a logarithmic relation, and the accuracy of the gas flow obtained according to the above-mentioned relation can be guaranteed.

Step 202, a target relational expression corresponding to the current pressure value is found in a preset list according to the current pressure value, wherein the preset list comprises a plurality of pressure values and relational expressions corresponding to the plurality of pressure values, and each of the relational expressions corresponding to the plurality of pressure values is a relational expression between operating parameters of the draught fan and a gas flow output by the positive pressure ventilation therapy machine.

The relational expression between each of operating parameters, corresponding to the different pressure values, of the draught fan and the gas flow output by the positive pressure ventilation therapy machine is obtained through a plurality of experiments, and thus, the preset list comprising the plurality of pressure values and the relational expressions corresponding to the plurality of pressure values is obtained. The current pressure value is found in the preset list pre-stored in advance according to the current pressure value. When the current pressure value is found in the preset list, a relational expression corresponding to the current pressure value is extracted as the target relational expression for subsequent calculation.

Step 203, a current gas flow output by the positive pressure ventilation therapy machine is determined according to the current operating parameter and the target relational expression.

Calculation is performed according to $$F = \frac{1}{B}\ln\left(\frac{P}{K}\right)$$

to obtain the current gas flow output by the positive pressure ventilation therapy machine, wherein F is the gas flow, P is the current operating parameter, B and K are conversion coefficients, and the conversion coefficients are related to the current pressure value.

As shown in parts of the preset list in FIG. 1, values, corresponding to the different pressure values, of B and K in the relational expression can be different. For example, B and K are correspondingly 206.48 and 0.15 when the pressure value is 4. When the draught fan is driven at the current operating parameter such as a constant voltage, the current current value of the draught fan is substituted into the above-mentioned formula, when the draught fan is driven at a constant current, the current voltage value of the draught fan is substituted into the above-mentioned formula, and thus, the gas flow output by the positive pressure ventilation therapy machine is obtained.

TABLE 1

| Pressure value | B | K |
| --- | --- | --- |
| 4 | 206.48 | 0.15 |
| 9 | 444.97 | 0.121 |

TABLE 1-continued

| Pressure value | B | K |
| --- | --- | --- |
| 15 | 686.38 | 0.1055 |
| 20 | 944.85 | 0.0964 |

According to the embodiment of the present invention, the current pressure value detected by a pressure sensor existing in the prior art is utilized, and the current gas flow output by the positive pressure ventilation therapy machine is determined according to the current operating parameter and the current pressure value of the draught fan as well as the preset list, so that the cost of the flow sensor specially used for measuring the gas flow and required by the positive pressure ventilation therapy machine is reduced, and the burden of a patient is relieved.

In an implementation manner of the present invention, the corresponding current gas flow can be obtained by adopting linear relation fitting in the prior art when the acquired current pressure value is not in the preset list. The specific processing way is:

1) two relational expressions corresponding to two pressure values adjacent to the current pressure value are found in the preset list, and the two relational expressions are determined as a first relational expression and a second relational expression when the current pressure value is not found in the preset list.

When the current pressure value is not found in the preset list, firstly, two pressure values adjacent to the current pressure value are found in the preset list, namely two pressure values of which one adjacent to the current pressure value is smaller than the current pressure value and the other is greater than the current pressure value and two relational expressions corresponding to the two pressure values are found in the preset list, and the two relational expressions are determined as the first relational expression and the second relational expression. With table 1 as an example, when the acquired current pressure value is 7, the current pressure value is not in table 1, then, two pressure values 4 and 9 adjacent to 7 as well as B and K corresponding to the pressure values 4 and 9 can be found.

2) A first gas flow and a second gas flow are determined according to the current operating parameter, the first relational expression and the second relational expression.

The current operating parameter such as the current current value or current voltage value of the draught fan is substituted into the first relational expression and the second relational expression to obtain the first gas flow and the second gas flow. For example, after it is acquired that B corresponding to the pressure value 4 is 206.48, K corresponding to the pressure value 4 is 0.15, B corresponding to the pressure value 9 is 444.97 and K corresponding to the pressure value 9 is 0.121, the current current value or the current voltage value of the draught fan is substituted into the first relational expression corresponding to the pressure value 4 and the second relational expression corresponding to the pressure value 9 to obtain the first gas flow and the second gas flow.

3) A mean value of the first gas flow and the second gas flow is determined as the current gas flow output by the positive pressure ventilation therapy machine.

A gas flow corresponding to a pressure value not existing in the preset list can also be obtained in the above-mentioned linear relation fitting way.

Figure 3:
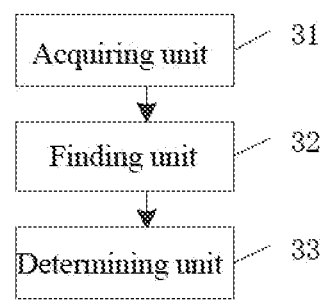
FIG. 3 is a structural diagram of a data processing device based on a positive pressure ventilation therapy machine provided by an embodiment of the present invention.

According to the embodiment of the present invention, the problem that the cost of the positive pressure ventilation therapy machine is increased due to the demand of installing the flow sensor for measuring the gas flow is solved. In addition, in the prior art, the gas flow is measured by adopting two pressure sensors instead of the flow sensor, which can also increase the additional expense, however, in the embodiment of the present invention, the gas flow can be obtained according to a self-existent parameter and a preset relational expression. In addition, compared with the prior art in which the way of calculating the gas flow according to the rotating speed and pressure value of the draught fan is adopted to result in the situation of inaccurate simulation for the gas flow when the characteristic curve of the draught fan is not monotonous, the embodiment of the present invention has the advantages that the rotating speed and electromagnetic torque of the draught fan have monotonicity under the condition that the voltage or current of the draught fan is unchanged, and the electromagnetic torque can be in direct proportion to the gas flow, so that the relation between the gas flow and the voltage or current of the draught fan is approximate to the logarithmic relation, and the accuracy of the gas flow obtained according to the above-mentioned relation can be guaranteed. Accordingly, FIG. 3 is a structural diagram of a data processing device based on a positive pressure ventilation therapy machine provided by an embodiment of the present invention. As shown in FIG. 3, the device comprises:

an acquiring unit 31, used for acquiring a current operating parameter and a current pressure value of a draught fan in the positive pressure ventilation therapy machine;

a finding unit 32, used for finding a target relational expression corresponding to the current pressure value in a preset list according to the current pressure value, wherein the preset list comprises a plurality of pressure values and relational expressions corresponding to the plurality of pressure values, and each of the relational expressions corresponding to the plurality of pressure values is a relational expression between operating parameters of the draught fan and a gas flow output by the positive pressure ventilation therapy machine; and a determining unit 33, used for determining a current gas flow output by the positive pressure ventilation therapy machine according to the current operating parameter and the target relational expression.

According to the embodiment of the present invention, the current gas flow output by the positive pressure ventilation therapy machine is determined according to the current operating parameter and the current pressure value of the draught fan as well as the preset list, so that the cost of the flow sensor specially used for measuring the gas flow and required by the positive pressure ventilation therapy machine is reduced, and the burden of a patient is relieved.

Further, the current operating parameter acquired by the acquiring unit is a current current value or a current voltage value.

Further, the determining unit is further used for performing calculation according to $$F = \frac{1}{B}\ln\left(\frac{P}{K}\right)$$

to obtain the current gas flow output by the positive pressure ventilation therapy machine, wherein F is the gas flow, P is the current operating parameter, B and K are conversion coefficients, and the conversion coefficients are related to the current pressure value.

Further, the finding unit is further used for finding two relational expressions corresponding to two pressure values adjacent to the current pressure value in the preset list and determining the two relational expressions as a first relational expression and a second relational expression when the current pressure value is not found in the preset list; and the determining unit is further used for determining a first gas flow and a second gas flow according to the current operating parameter, the first relational expression and the second relational expression and determining a mean value of the first gas flow and the second gas flow as the current gas flow output by the positive pressure ventilation therapy machine.

Various units in the data processing device based on the positive pressure ventilation therapy machine in the embodiment of the present invention are used for executing the corresponding steps of the data processing method based on the positive pressure ventilation therapy machine described in the above-mentioned embodiment to achieve the same or similar technical effect with the above-mentioned data processing method based on the positive pressure ventilation therapy machine, and therefore, more details of the data processing device based on the positive pressure ventilation therapy machine in the present embodiment can refer to the description of the data processing method based on the positive pressure ventilation therapy machine in the above-mentioned embodiment, the descriptions of the same content are omitted herein.

Accordingly, an embodiment of the present invention further provides a data processing device based on a positive pressure ventilation therapy machine, comprising a processor, a memory and a computer program stored in the memory and capable of operating on the processor, and the computer program implements the steps of the data processing method based on the positive pressure ventilation therapy machine in the above-mentioned embodiment when being executed by the processor.

Accordingly, an embodiment of the present invention further provides a computer readable storage medium, storing a computer program, and the computer program implements the steps of the data processing method based on the positive pressure ventilation therapy machine in the above-mentioned embodiment when being executed by a processor.

Optional implementation manners of the embodiments of the present invention are described in detail above in combination with the accompanying drawings, however, the embodiments of the present invention are not limited to the concrete details in the above-mentioned implementation manners, the technical solutions in the embodiments of the present invention can be subjected to various simple modifications within the scope of the technical concept of the embodiments of the present invention, and these simple modifications fall within the protective scope of the embodiments of the present invention.

It should be additionally explained that all specific technical features described in the above-mentioned specific implementation manners can be combined without conflicts in any appropriate ways. In order to avoid unnecessary repetition, various possible combination ways are not otherwise specified in the embodiments of the present invention.

The skilled in the art can understand that all or parts of steps of the method in the above-mentioned embodiment can be completed by related hardware instructed by a program, the program is stored in a storage medium and comprises a plurality of instructions for causing a single chip microcomputer, a chip or a processor to execute all or parts of the steps of the method in each of the embodiments of the present application. The above-mentioned storage medium comprises various media, such as a USB disk, a mobile hard disk, a Read-Only Memory (ROM), a Random Access Memory (RAM), a diskette or an optical disc, capable of storing program codes.

In addition, various different implementation manners of the embodiments of the present invention can also be arbitrarily combined and should also be regarded as contents disclosed in the embodiments of the present invention as long as they obey the concepts of the embodiments of the present invention.

The invention claimed is:

1. A method for determining a flow of a positive pressure ventilation therapy machine, the method implemented on the positive pressure ventilation therapy machine and comprising:

acquiring a current operating parameter of the positive pressure ventilation therapy machine;

acquiring a current pressure value for a draught fan of the positive pressure ventilation therapy machine from a sensor;

finding a target relational expression corresponding to the current pressure value in a preset list according to the current pressure value, wherein the preset list comprises a plurality of pressure values and relational expressions corresponding to the plurality of pressure values, and each of the relational expressions corresponding to the plurality of pressure values is a relational expression between operating parameters of the draught fan and a gas flow output by the positive pressure ventilation therapy machine; and determining a current gas flow output by the positive pressure ventilation therapy machine according to the current operating parameter and the target relational expression;

wherein the step of determining the current gas flow output by the positive pressure ventilation therapy machine according to the current operating parameter and the target relational expression comprises:

performing a calculation according to $$F = \frac{1}{B}\ln\left(\frac{P}{K}\right)$$

obtain the current gas flow output by the positive pressure ventilation therapy machine, wherein F is the gas flow, P is the current operating parameter, B and K are conversion coefficients, and the conversion coefficients are related to the current pressure value.

2. The method for determining the flow of the positive pressure ventilation therapy machine according to claim 1, wherein the current operating parameter is a current current value or a current voltage value.

3. The method for determining the flow of the positive pressure ventilation therapy machine according to claim 1, the method further comprising:

determining the current gas flow output by the positive pressure ventilation therapy machine by adopting linear relation fitting when the current pressure value is not found in the preset list.

4. The method for determining the flow of the positive pressure ventilation therapy machine according to claim 3, wherein the step of determining the current gas flow output by the positive pressure ventilation therapy machine by adopting linear relation fitting when the current pressure value is not found in the preset list comprises:

finding two relational expressions corresponding to two pressure values adjacent to the current pressure value in the preset list and determining the two relational expressions as a first relational expression and a second relational expression when the current pressure value is not found in the preset list;

determining a first gas flow and a second gas flow according to the current operating parameter, the first relational expression and the second relational expression; and determining a mean value of the first gas flow and the second gas flow as the current gas flow output by the positive pressure ventilation therapy machine.

5. A device for determining a flow in a positive pressure ventilation therapy machine, comprising:

a sensor that measures a current pressure value for a draught fan of the positive pressure ventilation machine;

a processor; and a memory, wherein a computer program capable of operating on the processor is stored in the memory; and the processor is communicatively coupled to the sensor and the memory, wherein, the processor is configured to:

acquire a current operating parameter of the positive pressure ventilation therapy machine;

acquire the current pressure value for the draught fan of the positive pressure ventilation therapy machine;

find a target relational expression corresponding to the current pressure value in a preset list according to the current pressure value, wherein the preset list comprises a plurality of pressure values and relational expressions corresponding to the plurality of pressure values, and each of the relational expressions corresponding to the plurality of pressure values is a relational expression between operating parameters of the draught fan and a gas flow output by the positive pressure ventilation therapy machine; and determine a current gas flow output by the positive pressure ventilation therapy machine according to the current operating parameter and the target relational expression;

wherein the current gas flow output by the positive pressure ventilation therapy machine is determined according to the current operating parameter and the target relational expression comprises:

performing a calculation according to $$F = \frac{1}{B}\ln\left(\frac{P}{K}\right)$$

to obtain the current gas flow output by the positive pressure ventilation therapy machine, wherein F is the gas flow, P is the current operating parameter, B and K are conversion coefficients, and the conversion coefficients are related to the current pressure value.

6. The device for determining the flow of the positive pressure ventilation therapy machine according to claim 5, wherein the current operating parameter is a current current value or a current voltage value.

7. The device for determining the flow of the positive pressure ventilation therapy machine according to claim 5, wherein the processor is further configured to determine the current gas flow output by the positive pressure ventilation therapy machine by adopting linear relation fitting when the current pressure value is not found in the preset list.

8. The device for determining the flow of the positive pressure ventilation therapy machine according to claim 7, wherein determining the current gas flow output by the positive pressure ventilation therapy machine by adopting linear relation fitting when the current pressure value is not found in the preset list comprises:

finding two relational expressions corresponding to two pressure values adjacent to the current pressure value in the preset list and determining the two relational expressions as a first relational expression and a second relational expression when the current pressure value is not found in the preset list;

determining a first gas flow and a second gas flow according to the current operating parameter, the first relational expression and the second relational expression; and determining a mean value of the first gas flow and the second gas flow as the current gas flow output by the positive pressure ventilation therapy machine.

\* \* \* \* \*